US005767244A

United States Patent [19]
Goeddel et al.

[11] Patent Number: 5,767,244
[45] Date of Patent: Jun. 16, 1998

[54] PROTEIN-TRAF6

[75] Inventors: David V. Goeddel, Hillsborough; Jessie Xiong, Foster City, both of Calif.

[73] Assignee: Tularik Inc., South San Francisco, Calif.

[21] Appl. No.: 975,405

[22] Filed: Nov. 20, 1997

Related U.S. Application Data

[62] Division of Ser. No. 639,237, Apr. 19, 1996, Pat. No. 5,710,013.

[51] Int. Cl.⁶ .............................................. C07K 14/705
[52] U.S. Cl. ........................ 530/350; 435/7.1; 435/7.2; 436/501
[58] Field of Search ..................... 435/7.1, 7.2, 64.1; 530/350; 436/501

[56] References Cited

U.S. PATENT DOCUMENTS 5,710,013  1/1998  Goeddel et al. ........................ 435/29

OTHER PUBLICATIONS

Rothe et al. "TRAF2–mediated activation of NF–kappaB by TNF receptor 2 and CD40". Science 269:1424–1429, Sep. 1995.

*Primary Examiner*—John Ulm
*Attorney, Agent, or Firm*—Richard Aron Osman

[57] ABSTRACT

The invention provides methods and compositions relating to a novel tumor necrosis factor receptor associated factor number six (TRAF6) protein, which transcriptionally activates Nuclear Factor κB. The invention provides isolated TRAF6 hybridization probes and primers capable of hybridizing with the disclosed TRAF6 gene, nucleic acids encoding the subject TRAF6 proteins, methods of making the subject TRAF6 proteins, and methods of using the subject compositions in diagnosis and drug screening.

5 Claims, 2 Drawing Sheets

10,767,244

PROTEIN-TRAF6

This is a division of application Ser. No. 08/639,237 filed Apr. 19, 1996, now U.S. Pat. No. 5,710,013.

FIELD OF THE INVENTION

The field of this invention is a class of human proteins involved in transcription and immuno-regulation.

BACKGROUND

Nuclear factor κB (NF-κB) is a homo- or heterodimer of members of the Rel family of transcriptional activators that is involved in the inducible expression of a wide variety of important cellular genes including numerous cytokines, cytokine receptors, major histocompatibility antigens, serum amyloid A protein, etc. as well as many viral genes including genes of HIV, SV40, cytomegalovirus, etc.

Several tumor necrosis factor receptor-associated factor (TRAF) proteins have been identified and shown to be involved in the signaling of various cellular responses including cytotoxicity, anti-viral activity, immuno-regulatory activities and the transcriptional regulation of a number of genes.

Accordingly, the ability to exogenously modulate the activity of NF-κB and/or TRAF proteins would yield therapeutic application for numerous clinical indications. In addition, components of such pathways would provide valuable target reagents for automated, cost-effective, high throughput drug screening assays and hence would have immediate application in domestic and international pharmaceutical and biotechnology drug development programs. The present invention provides novel TRAF proteins which regulate NF-κB expression, their use in drug screens, and nucleic acids encoding the same.

Relevant Literature

Rothe et al. (1994) Cell 78, 681–692 report that NF-κB expression can be mediated by the 75–80 kDa TNF receptor (TNF-R2), that a short region of the 78 amino acids at the C-terminus of the cytoplasmic domain of TNF-R2 is required for signaling NF-κB activation, and that this region binds to closely related putative effectors, TRAF1 and TRAF2, see also, Hsu et al. (1995) Cell 81, 495 and Rothe et al., pending U.S. patent application Ser. No: 08/446,915. A third distinct TRAF, TRAF3, has been reported by Huet al. (1994) J. Biol Chem 269, 30069; Cheng et al. (1995) Science 267, 1494–1498; Mosialos et al. (1995) Cell 80, 389; and Sato et al. (1995) FEBS Letters, 358, 113. Rothe et al. (1995) Science 269, 1424–1427 report TRAF2- (but not TRAF1- or 3-) mediated activation of NF-κB by TNF-R2 and CD40.

SUMMARY OF THE INVENTION

The invention provides methods and compositions relating to a novel tumor necrosis factor receptor associated factor number six (TRAF6) protein and gene. The subject TRAF6 proteins are encoded by cDNAs which hybridizes with SEQ ID NO:01 under high stringency conditions; specifically bind a natural intracellular TRAF6 binding target and comprise the amino sequence of SEQ ID NO:2 or fragment thereof sufficient to specifically bind a natural intracellular TRAF6 binding target.

The invention also provides isolated TRAF6 hybridization probes and primers capable of hybridizing with the disclosed TRAF6 cDNA, nucleic acids encoding the subject TRAF6 proteins, methods of making the subject TRAF6 proteins, and methods of using the subject compositions in diagnosis (e.g. genetic hybridization screens for TRAF6 gene mutations), and in the biopharmaceutical industry (e.g. reagents for screening chemical libraries for lead compounds for a pharmacological agent useful in the diagnosis or treatment of disease associated with immune regulation).

DETAILED DESCRIPTION OF THE INVENTION

Figure 1:
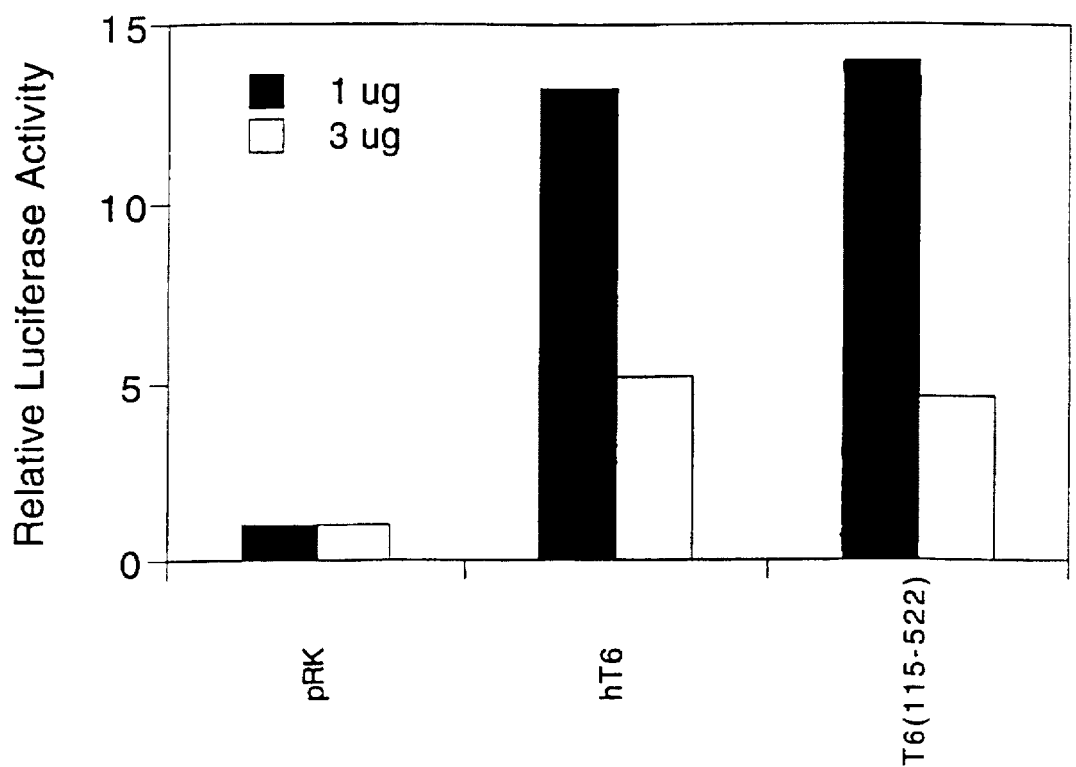
FIG. 1 shows shows the effect of coexpression of a TRAF6 deletion mutant on NF-κB-dependent reporter gene activation by TRAF6.

The nucleotide sequence of a natural cDNA encoding human TRAF6 is shown as SEQ ID NO:1 and the full conceptual translate shown as SEQ ID NO:2. The TRAF6 proteins of the invention include incomplete translates of SEQ ID NO:1 and deletion mutants of SEQ ID NO:2, which translates and deletions mutants have TRAF6-specific activity.

TRAF6-specific activity or function may be determined by convenient in vitro, cell-based, or in vivo assays. Preferred proteins are capable of modulating NF-κB activation. Such activity or function may be demonstrated in cell culture (e.g. cell transfections) or in animals (e.g. in vivo gene therapy, transgenics). TRAF6 specific function can also be demonstrated by specific binding to a TRAF6 specific binding target, including natural binding targets such as TRAF6 (dimerization) and nonnatural targets such as TRAF6-specific antibodies. Finally, specific function can be assayed immunologically by the ability of the subject protein to elicit a TRAF6 specific antibody in a rodent or rabbit. TRAF6-specificity of the binding agent may be shown at a populational level by binding equilibrium constants (usually at least about $10^7 M^{-1}$, preferably at least about $10^8 M^{-1}$, more preferably at least about $10^9 M^{-1}$). A wide variety of cell-based and cell-free assays may be used to demonstrate TRAF6-specific binding; preferred are rapid in vitro, cell-free assays such as mediating or inhibiting TRAF6-protein (e.g. TRAF6-TRAF6, TRAF2 or TRAF3) binding, immunoassays, etc. In any event, TRAF6 specificity necessarily distinguishes the subject TRAF6 protein from TRAF1-5.

The claimed TRAF6 proteins are isolated or pure and are typically recombinantly produced. An "isolated" protein for example, is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. A wide variety of molecular and biochemical methods are available for generating, expressing and purifying the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides TRAF6-specific binding agents, methods of identifying and making such agents, and their use in diagnosis, therapy and pharmaceutical development. For example, TRAF6-specific agents are useful in a variety of diagnostic and therapeutic applications, especially where disease or disease prognosis is associated with improper utilization of a pathway involving TRAF6, e.g. NF-κB activation. Novel TRAF6-specific binding agents include TRAF6-specific antibodies and other natural intracellular binding agents identified with assays such as one- and two-hybrid screens, non-natural intracellular binding agents identified in screens of chemical libraries such as describe below, etc.

The invention also provides nucleic acids encoding the subject proteins, which nucleic acids may be part of TRAF6-expression vectors and may be incorporated into recombinant cells for expression and screening, transgenic animals for functional studies (e.g. the efficacy of candidate drugs for disease associated with TRAF6-mediated signal transduction), etc., and nucleic acid hybridization probes and replication/amplification primers having a TRAF6 cDNA specific sequence contained in SEQ ID NO:1 and sufficient to effect specific hybridization thereto (i.e. will specifically hybridize with TRAF6 cDNA (SEQ ID NO:1) in the presence of TRAF1-5 20 cDNA). Demonstrating specific hybridization generally requires high-stringency conditions, for example, hybridizing in a buffer comprising 30% formamide in 5×SSPE (0.18M NaCl, 0.01M NaPO$_4$, pH7.7, 0.001M EDTA) buffer at a temperature of 42° C. and remaining bound when subject to washing at 42° C. with 0.2× SSPE; preferably hybridizing in a buffer comprising 50% formamide in 5× SSPE buffer at a temperature of 42° C. and remaining bound when subject to washing at 42° C. with 0.2× SSPE buffer at 42° C. In any event, TRAF6 specific hybridization probes and primers necessarily distinguish TRAF6 cDNA from cDNA's encoding TRAF 1-5. TRAF6 cDNA homologs can also be characterized by BLASTX (Altschul et al. (1990) Basic Local Alignment Search Tool, J Mol Biol 215, 403–410) probability scores. Using this nucleic acid sequence search program BLASTX, complete coding region TRAF6 cDNA homologs provide a Probability P(N) score of less than $1.0e^{-200}$.

The subject nucleic acids are isolated, i.e. unaccompanied by at least some of the material with which it is associated in its natural state, preferably constituting at least about 0.5%, preferably at least about 5% by weight of total nucleic acid present in a given fraction. The subject nucleic acids find a wide variety of applications including use as translatable transcripts, hybridization probes, PCR primers, diagnostic nucleic acids, etc.; use in detecting the presence of TRAF6 genes and gene transcripts and in detecting or amplifying nucleic acids encoding additional TRAF6 homologs and structural analogs. When used as expression constructs, the nucleic acids are usually recombinant, meaning they comprise a sequence joined to a nucleotide other than that which it is joined to on a natural chromosome. The subject nucleic acids may be contained within vectors, cells or organisms.

In diagnosis, TRAF6 hybridization probes and/or primers find use in identifying wild-type and mutant TRAF6 alleles in clinical and laboratory samples. Mutant alleles are used to generate allele-specific oligonucleotide (ASO) probes for high-throughput clinical diagnoses.

The invention provides efficient methods of identifying agents, compounds or lead compounds for agents active at the level of a TRAF6 modulatable cellular function. Generally, these screening methods involve assaying for compounds which modulate a TRAF6 interaction with a natural TRAF6 binding target. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications may include infection, genetic disease, cell growth and regulatory disfunction, such as neoplasia, inflammation, hypersensitivity, etc.

A wide variety of assays for binding agents are provided including protein-protein binding assays, immunoassays, cell based assays, etc. A preferred assay is a high-through put in vitro binding assay. Here, the TRAF6 compositions may be part of a fusion product with another peptide or polypeptide, e.g. a polypeptide that is capable of providing or enhancing protein-protein binding, stability under assay conditions, or a tag for detection or anchoring, etc. The assay mixtures comprise a natural intracellular TRAF6 binding target such as TRAF2, TRAF3 or TRAF6. While native binding targets may be used, it is frequently preferred to use portions (e.g. peptides, nucleic acid fragments) thereof so long as the portion provides binding affinity and avidity to the subject TRAF6 conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the TRAF6 specifically binds the cellular binding target, portion or analog with a reference binding affinity. The mixture components can be added in any order that provides for the requisite bindings and incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the agent-biased binding between the TRAF6 and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). In addition, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

A difference in the binding affinity of the TRAF6 protein to the target in the absence of the agent as compared with the binding affinity in the presence of the agent indicates that the agent modulates the binding of the TRAF6 protein to the TRAF6 binding target. Analogously, in the cell-based transcription assay also described below, a difference in the TRAF6 transcriptional induction in the presence and absence of an agent indicates the agent modulates TRAF6-induced transcription. A difference, as used herein, is statistically significant and preferably represents at least a 50%, more preferably at least a 90% difference.

The following experiments and examples are offered by way of illustration and not by way of limitation.

EXPERIMENTAL

The human TRAF6 cDNA of SEQ ID NO:1 was cloned from human spleen cell and human umbilical vein endothelial cell cDNA libraries by high stringency hybridization: hybridization in 40% formamide, 5% Dextran sulfate, 0.5% SDS, 5× SSPE at 42° C. followed by washes in 2× SSPE, 0.1% SDS at 25° C. and in 0.1× SSPE, 0.1% SDS at 42° C.; using TRAF oligonucleotide probes.

The resultant cDNA (SEQ ID NO:1) encodes human TRAF6 (SEQ ID NO:2). In cotransfection experiments, TRAF6 was shown to activate an NF-κB-dependent reporter gene, see FIG. 1.

A yeast two-hybrid system was used to identify TRAF2, TRAF3 and TRAF6 as an intracellular binding targets of the TRAF6 protein of SEQ ID NO:2. A transfection based co-immunoprecipitation assay was also used to identify intracellular binding targets of the TRAF6 protein of SEQ ID NO:2. Briefly, FLAG-tagged TRAF1, 2, 3, 4 and 6 were cotransfected with HA-tagged TRAF6. Lysates were immunoprecipitated with anti-HA antibody and proteinA glass beads. Western blot analysis using an anti-FLAG antibody revealed TRAF6-TRAF6 and TRAF6-TRAF3 complexes.

Figure 2:
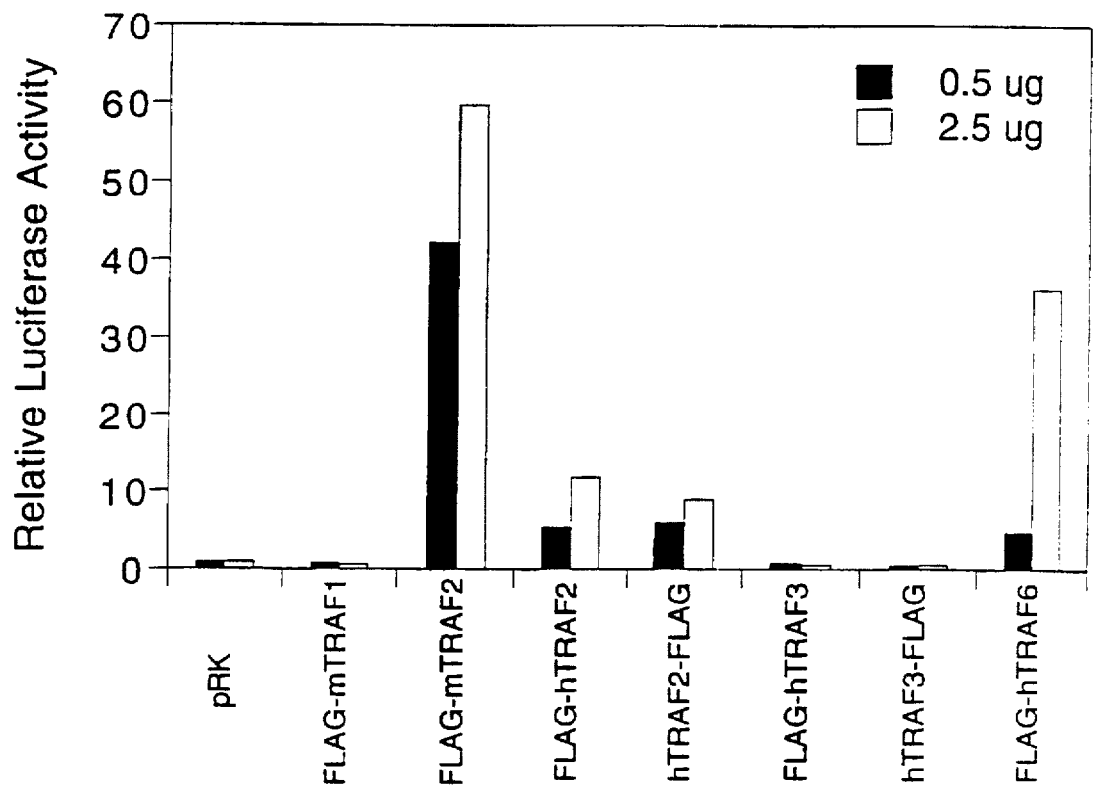
FIG. 2 NF-κB-dependent reporter gene activation by TRAF proteins.

Deletion mutagenesis of TRAF6 indicate that residues 115–522 are sufficient to mediate activation of NF-κB, see FIG. 2. In contrast, continuing the 5' deletion to the second Zn finger domain abolished activity; as did 5' deletions through all five Zn finger domains, and deletions through the C domain. Similarly, an internal deletion of the Zn finger domains abolished activity.

EXAMPLES

1. Protocol for High-Throughput Human TRAF6-TRAF6 Binding Assay

A. Reagents

Neutralite Avidin: 20 µg/ml in PBS.

Blocking buffer: 5% BSA, 0.5% Tween 20 in PBS; 1 hour at room temperature.

Assay Buffer: 100 mM KCl, 20 mM HEPES pH 7.6, 0.25 mM EDTA, 1% glycerol, 0.5% NP-40, 50 mM β-mercaptoethanol, 1 mg/ml BSA, cocktail of protease inhibitors.

$^{33}$P human TRAF6 (SEQUENCE ID NO:2, residues 1–522) 10× stock: $10^{-8}$–$10^{-6}$M unlabeled human TRAF6 supplemented with 200,000–250,000 cpm of labeled human TRAF6 (Beckman counter). Place in the 4° C. microfridge during screening.

Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

ΔTRAF6: $10^{-8}$–$10^{-5}$M biotinylated truncated ΔTRAF6 (SEQUENCE ID NO:2, residues 115–522) in PBS.

B. Preparation of Assay Plates

Coat with 120 µl of stock N-Avidin per well overnight at 4° C.

Wash 2 times with 200 µl PBS.

Block with 150 µl of blocking buffer.

Wash 2 times with 200 µl PBS.

C. Assay

Add 40 µl assay buffer/well.

Add 10 µl compound or extract.

Add 10 µl $^{33}$P-human TRAF6 (20,000–25,000 cpm/0.1–10 pmoles/well=$10^{-9}$–$10^{-7}$M final concentration).

Shake at 25° C. for 15 minutes.

Incubate additional 45 minutes at 25° C.

Add 40 µl biotinylated truncated ΔTRAF6 (0.1–10 pmoles/40 µl in assay buffer)

Incubate 1 hour at room temperature.

Stop the reaction by washing 4 times with 200 µl PBS.

Add 150 µl scintillation cocktail.

Count in Topcount.

D. Controls for all Assays (Located on Each Plate)

a. Non-specific binding b. Soluble (non-biotinylated truncated ΔTRAF6) at 80% inhibition.

2. Protocol for NF-κB-Dependent Reporter Gene Assay 293 cells are transiently co-transfected with an E-selectin-luciferase reporter gene plasmid (Schindler et al. (1994) Mol Cell Biol 14, 5820) and TRAF6 expression vectors containing the TRAF6 coding region (see, SEQUENCE ID NO:1) produced as described for TRAF1, 2 and 3 in Rothe et al. (1995) Science 269, 1424.

Control cells are transiently co-transfected with a CMV promoter luciferase reporter gene plasmid and/or TRAF2 expression vectors as described supra.

The transfected cells are incubated 24 hours in the presence of the candidate compound or extract and then the cells harvested and luciferase activities determined and normalized on the basis of β-galactosidase expression, as described in FIG. 3B of Rothe et al. (1995) Science 269, 1424.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising an amino acid sequence selected from the group consisting of SEQ ID NO:2 residues 1–114 of SEQ ID NO:2 and residues 115–522 of SEQ ID NO:2.

2. An isolated polypeptide according to claim 1, wherein said polypeptide comprises at least a portion of the amino sequence of SEQ ID NO:2, said portion comprising SEQ ID NO:2, residues 1–114.

3. An isolated polypeptide according to claim 1, wherein said polypeptide comprises at least a portion of the amino sequence of SEQ ID NO:2, said portion comprising SEQ ID NO:2, residues 115–522.

4. A method of screening for an agent which modulates the binding of a tumor necrosis factor receptor associated factor number six (TRAF6) polypeptide to a natural intracellular TRAF6 binding target, said method comprising the steps of:

incubating a mixture comprising:
      an isolated polypeptide according to claim 1,
      a natural intracellular binding target of said polypeptide, wherein said binding target is capable of specifically binding said polypeptide, and
      a candidate agent;
   under conditions whereby, but for the presence of said agent, said polypeptide specifically binds said binding target at a reference affinity;
   detecting the binding affinity of said polypeptide to said binding target to determine an agent-biased affinity,
   wherein a difference between the agent-biased affinity and the reference affinity indicates that said agent modulates the binding of said polypeptide to said binding target.

5. A method according to claim 4, wherein said binding target comprises a tumor necrosis factor receptor associated factor or fragment thereof sufficient to specifically bind said isolated polypeptide.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2248 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 230..1795

( x i ) SEQUENCE DESCRIPTION: SEQ ID NO:1:

```
GGCACGAGCC GCAGCTGGGG CTTGGCCTGC GGGCGGCCAG CGAAGGTGGC GAAGGCTCCC      60

ACTGGATCCA GAGTTTGCCG TCCAAGCAGC CTCGTCTCGG CGCGCAGTGT CTGTGTCCGT     120

CCTCTACCAG CGCCTTGGCT GAGCGGAGTC GTGCGGTTGG TGGGGGAGCC CTGCCCTCCT     180

GGTTCGGCCT CCCCGCGCAC TAGAACGAGC AAGTGATAAT CAAGTTACT ATG AGT        235
                                                     Met Ser
                                                      1

CTG CTA AAC TGT GAA AAC AGC TGT GGA TCC AGC CAG TCT GAA AGT GAC      283
Leu Leu Asn Cys Glu Asn Ser Cys Gly Ser Ser Gln Ser Glu Ser Asp
          5                  10                  15

TGT TGT GTG GCC ATG GCC AGC TCC TGT AGC GCT GTA ACA AAA GAT GAT      331
Cys Cys Val Ala Met Ala Ser Ser Cys Ser Ala Val Thr Lys Asp Asp
     20                  25                  30

AGT GTG GGT GGA ACT GCC AGC ACG GGG AAC CTC TCC AGC TCA TTT ATG      379
Ser Val Gly Gly Thr Ala Ser Thr Gly Asn Leu Ser Ser Ser Phe Met
 35                  40                  45                  50

GAG GAG ATC CAG GGA TAT GAT GTA GAG TTT GAC CCA CCC CTG GAA AGC      427
Glu Glu Ile Gln Gly Tyr Asp Val Glu Phe Asp Pro Pro Leu Glu Ser
                 55                  60                  65

AAG TAT GAA TGC CCC ATC TGC TTG ATG GCA TTA CGA GAA GCA GTG CAA      475
Lys Tyr Glu Cys Pro Ile Cys Leu Met Ala Leu Arg Glu Ala Val Gln
             70                  75                  80

ACG CCA TGC GGC CAT AGG TTC TGC AAA GCC TGC ATC ATA AAA TCA ATA      523
Thr Pro Cys Gly His Arg Phe Cys Lys Ala Cys Ile Ile Lys Ser Ile
         85                  90                  95

AGG GAT GCA GGT CAC AAA TGT CCA GTT GAC AAT GAA ATA CTG CTG GAA      571
Arg Asp Ala Gly His Lys Cys Pro Val Asp Asn Glu Ile Leu Leu Glu
    100                 105                 110

AAT CAA CTA TTT CCA GAC AAT TTT GCA AAA CGT GAG ATT CTT TCT CTG      619
Asn Gln Leu Phe Pro Asp Asn Phe Ala Lys Arg Glu Ile Leu Ser Leu
115                 120                 125                 130

ATG GTG AAA TGT CCA AAT GAA GGT TGT TTG CAC AAG ATG GAA CTG AGA      667
Met Val Lys Cys Pro Asn Glu Gly Cys Leu His Lys Met Glu Leu Arg
                135                 140                 145

CAT CTT GAG GAT CAT CAA GCA CAT TGT GAG TTT GCT CTT ATG GAT TGT      715
His Leu Glu Asp His Gln Ala His Cys Glu Phe Ala Leu Met Asp Cys
            150                 155                 160

CCC CAA TGC CAG CGT CCC TTC CAA AAA TTC CAT ATT AAT ATT CAC ATT      763
Pro Gln Cys Gln Arg Pro Phe Gln Lys Phe His Ile Asn Ile His Ile
        165                 170                 175

CTG AAG GAT TGT CCA AGG AGA CAG GTT TCT TGT GAC AAC TGT GCT GCA      811
Leu Lys Asp Cys Pro Arg Arg Gln Val Ser Cys Asp Asn Cys Ala Ala
```

-continued

|     | 180 |     |     |     | 185 |     |     |     | 190 |     |     |     |     |      |
|-----|-----|-----|-----|-----|-----|-----|-----|-----|-----|-----|-----|-----|-----|------|
| TCA | ATG | GCA | TTT | GAA | GAT | AAA | GAG | ATC | CAT | GAC | CAG | AAC | TGT | CCT TTG | 859 |
| Ser | Met | Ala | Phe | Glu | Asp | Lys | Glu | Ile | His | Asp | Gln | Asn | Cys | Pro Leu |
| 195 |     |     |     | 200 |     |     |     | 205 |     |     |     |     |     | 210 |

| GCA | AAT | GTC | ATC | TGT | GAA | TAC | TGC | AAT | ACT | ATA | CTC | ATC | AGA | GAA CAG | 907 |
| Ala | Asn | Val | Ile | Cys | Glu | Tyr | Cys | Asn | Thr | Ile | Leu | Ile | Arg | Glu Gln |
|     |     |     |     | 215 |     |     |     | 220 |     |     |     |     |     | 225 |

| ATG | CCT | AAT | CAT | TAT | GAT | CTA | GAC | TGC | CCT | ACA | GCC | CCA | ATT | CCA TGC | 955 |
| Met | Pro | Asn | His | Tyr | Asp | Leu | Asp | Cys | Pro | Thr | Ala | Pro | Ile | Pro Cys |
|     |     |     | 230 |     |     |     |     | 235 |     |     |     | 240 |     |     |

| ACA | TTC | AGT | ACT | TTT | GGT | TGC | CAT | GAA | AAG | ATG | CAG | AGG | AAT | CAC TTG | 1003 |
| Thr | Phe | Ser | Thr | Phe | Gly | Cys | His | Glu | Lys | Met | Gln | Arg | Asn | His Leu |
|     |     | 245 |     |     |     |     | 250 |     |     |     |     | 255 |     |     |

| GCA | CGC | CAC | CTA | CAA | GAG | AAC | ACC | CAG | TCA | CAC | ATG | AGA | ATG | TTG GCC | 1051 |
| Ala | Arg | His | Leu | Gln | Glu | Asn | Thr | Gln | Ser | His | Met | Arg | Met | Leu Ala |
|     | 260 |     |     |     |     | 265 |     |     |     |     | 270 |     |     |     |

| CAG | GCT | GTT | CAT | AGT | TTG | AGC | GTT | ATA | CCC | GAC | TCT | GGG | TAT | ATC TCA | 1099 |
| Gln | Ala | Val | His | Ser | Leu | Ser | Val | Ile | Pro | Asp | Ser | Gly | Tyr | Ile Ser |
| 275 |     |     |     |     | 280 |     |     |     |     | 285 |     |     |     | 290 |

| GAG | GTC | CGG | AAT | TTC | CAG | GAA | ACT | ATT | CAC | CAG | TTA | GAG | GGT | CGC CTT | 1147 |
| Glu | Val | Arg | Asn | Phe | Gln | Glu | Thr | Ile | His | Gln | Leu | Glu | Gly | Arg Leu |
|     |     |     |     | 295 |     |     |     |     | 300 |     |     |     |     | 305 |

| GTA | AGA | CAA | GAC | CAT | CAA | ATC | CGG | GAG | CTG | ACT | GCT | AAA | ATG | GAA ACT | 1195 |
| Val | Arg | Gln | Asp | His | Gln | Ile | Arg | Glu | Leu | Thr | Ala | Lys | Met | Glu Thr |
|     |     |     | 310 |     |     |     |     | 315 |     |     |     | 320 |     |     |

| CAG | AGT | ATG | TAT | GTA | AGT | GAG | CTC | AAA | CGA | ACC | ATT | CGA | ACC | CTT GAG | 1243 |
| Gln | Ser | Met | Tyr | Val | Ser | Glu | Leu | Lys | Arg | Thr | Ile | Arg | Thr | Leu Glu |
|     |     | 325 |     |     |     |     | 330 |     |     |     |     | 335 |     |     |

| GAC | AAA | GTT | GCT | GAA | ATC | GAA | GCA | CAG | CAG | TGC | AAT | GGA | ATT | TAT ATT | 1291 |
| Asp | Lys | Val | Ala | Glu | Ile | Glu | Ala | Gln | Gln | Cys | Asn | Gly | Ile | Tyr Ile |
|     | 340 |     |     |     |     | 345 |     |     |     |     | 350 |     |     |     |

| TGG | AAG | ATT | GGC | AAC | TTT | GGA | ATG | CAT | TTG | AAA | TGT | CAA | GAA | GAG GAG | 1339 |
| Trp | Lys | Ile | Gly | Asn | Phe | Gly | Met | His | Leu | Lys | Cys | Gln | Glu | Glu Glu |
| 355 |     |     |     |     | 360 |     |     |     |     | 365 |     |     |     | 370 |

| AAA | CCT | GTT | GTG | ATT | CAT | AGC | CCT | GGA | TTC | TAC | ACT | GGC | AAA | CCC GGG | 1387 |
| Lys | Pro | Val | Val | Ile | His | Ser | Pro | Gly | Phe | Tyr | Thr | Gly | Lys | Pro Gly |
|     |     |     |     | 375 |     |     |     |     | 380 |     |     |     |     | 385 |

| TAC | AAA | CTG | TGC | ATG | CGC | TTG | CAC | CTT | CAG | TTA | CCG | ACT | GCT | CAG CGC | 1435 |
| Tyr | Lys | Leu | Cys | Met | Arg | Leu | His | Leu | Gln | Leu | Pro | Thr | Ala | Gln Arg |
|     |     |     | 390 |     |     |     |     | 395 |     |     |     | 400 |     |     |

| TGT | GCA | AAC | TAT | ATA | TCC | CTT | TTT | GTC | CAC | ACA | ATG | CAA | GGA | GAA TAT | 1483 |
| Cys | Ala | Asn | Tyr | Ile | Ser | Leu | Phe | Val | His | Thr | Met | Gln | Gly | Glu Tyr |
|     |     | 405 |     |     |     |     | 410 |     |     |     |     | 415 |     |     |

| GAC | AGC | CAC | CTC | CCT | TGG | CCC | TTC | CAG | GGT | ACA | ATA | CGC | CTT | ACA ATT | 1531 |
| Asp | Ser | His | Leu | Pro | Trp | Pro | Phe | Gln | Gly | Thr | Ile | Arg | Leu | Thr Ile |
| 420 |     |     |     |     | 425 |     |     |     |     | 430 |     |     |     |     |

| CTT | GAT | CAG | TCT | GAA | GCA | CCT | GTA | AGG | CAA | AAC | CAC | GAA | GAG | ATA ATG | 1579 |
| Leu | Asp | Gln | Ser | Glu | Ala | Pro | Val | Arg | Gln | Asn | His | Glu | Glu | Ile Met |
| 435 |     |     |     |     | 440 |     |     |     |     | 445 |     |     |     | 450 |

| GAT | GCC | AAA | CCA | GAG | CTG | CTT | GCT | TTC | CAG | CGA | CCC | ACA | ATC | CCA CGG | 1627 |
| Asp | Ala | Lys | Pro | Glu | Leu | Leu | Ala | Phe | Gln | Arg | Pro | Thr | Ile | Pro Arg |
|     |     |     |     | 455 |     |     |     |     | 460 |     |     |     |     | 465 |

| AAC | CCA | AAA | GGT | TTT | GGC | TAT | GTA | ACT | TTT | ATG | CAT | CTG | GAA | GCC CTA | 1675 |
| Asn | Pro | Lys | Gly | Phe | Gly | Tyr | Val | Thr | Phe | Met | His | Leu | Glu | Ala Leu |
|     |     |     | 470 |     |     |     |     | 475 |     |     |     |     | 480 |     |

| AGA | CAA | AGA | ACT | TTC | ATT | AAG | GAT | GAC | ACA | TTA | TTA | GTG | CGC | TGT GAG | 1723 |
| Arg | Gln | Arg | Thr | Phe | Ile | Lys | Asp | Asp | Thr | Leu | Leu | Val | Arg | Cys Glu |
|     |     |     |     | 485 |     |     |     | 490 |     |     |     |     | 495 |     |

| GTC | TCC | ACC | CGC | TTT | GAC | ATG | GGT | AGC | CTT | CGG | AGG | GAG | GGT | TTT CAG | 1771 |
| Val | Ser | Thr | Arg | Phe | Asp | Met | Gly | Ser | Leu | Arg | Arg | Glu | Gly | Phe Gln |

5,767,244

-continued

```
          500                    505                     510
CCA CGA AGT ACT GAT GCA GGG GTA TAGCTTGCCC TCACTTGCTC AAAAACAACT    1825
Pro Arg Ser Thr Asp Ala Gly Val
515                 520

ACCTGGAGAA AACAGTGCCT TTCCTTGCCC TGTTCTCAAT AACATGCAAA CAAACAAGCC   1885

ACGGGAAATA TGTAATATCT ACTAGTGAGT GTTGTTAGAG AGGTCACTTA CTATTTCTTC   1945

CTGTTACAAA TGATCTGAGG CAGTTTTTC CTGGGAATCC ACACGTTCCA TGCTTTTTCA    2005

GAAATGTTAG GCCTGAAGTG CCTGTGGCAT GTTGCAGCAG CTATTTTGCC AGTTAGTATA   2065

CCTCTTTGTT GTACTTTCTT GGGCTTTTGC TCTGGTGTAT TTATTGTCA GAAAGTCCAG    2125

ACTCAAGAGT ACTAAACTTT TAATAATAAT GGATTTTCCT TAAAACTTCA GTCTTTTTGT   2185

AGTATTATAT GTAATATATT AAAAGTGAAA ATCACTACCG CCTTGAAAAA AAAAAAAAA    2245

AAA                                                                2248
```

(2) INFORMATION FOR SEQ ID NO:2:

(i) SEQUENCE CHARACTERISTICS:
        (A) LENGTH: 522 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Leu Leu Asn Cys Glu Asn Ser Cys Gly Ser Ser Gln Ser Glu
 1               5                  10                  15

Ser Asp Cys Cys Val Ala Met Ala Ser Ser Cys Ser Ala Val Thr Lys
                20                  25                  30

Asp Asp Ser Val Gly Gly Thr Ala Ser Thr Gly Asn Leu Ser Ser Ser
            35                  40                  45

Phe Met Glu Glu Ile Gln Gly Tyr Asp Val Glu Phe Asp Pro Pro Leu
     50                  55                  60

Glu Ser Lys Tyr Glu Cys Pro Ile Cys Leu Met Ala Leu Arg Glu Ala
 65                  70                  75                  80

Val Gln Thr Pro Cys Gly His Arg Phe Cys Lys Ala Cys Ile Ile Lys
                85                  90                  95

Ser Ile Arg Asp Ala Gly His Lys Cys Pro Val Asp Asn Glu Ile Leu
            100                 105                 110

Leu Glu Asn Gln Leu Phe Pro Asp Asn Phe Ala Lys Arg Glu Ile Leu
            115                 120                 125

Ser Leu Met Val Lys Cys Pro Asn Glu Gly Cys Leu His Lys Met Glu
    130                 135                 140

Leu Arg His Leu Glu Asp His Gln Ala His Cys Glu Phe Ala Leu Met
145                 150                 155                 160

Asp Cys Pro Gln Cys Gln Arg Pro Phe Gln Lys Phe His Ile Asn Ile
                165                 170                 175

His Ile Leu Lys Asp Cys Pro Arg Arg Gln Val Ser Cys Asp Asn Cys
            180                 185                 190

Ala Ala Ser Met Ala Phe Glu Asp Lys Glu Ile His Asp Gln Asn Cys
            195                 200                 205

Pro Leu Ala Asn Val Ile Cys Glu Tyr Cys Asn Thr Ile Leu Ile Arg
    210                 215                 220

Glu Gln Met Pro Asn His Tyr Asp Leu Asp Cys Pro Thr Ala Pro Ile
225                 230                 235                 240

Pro Cys Thr Phe Ser Thr Phe Gly Cys His Glu Lys Met Gln Arg Asn
```

|     |     |     | 245 |     |     |     | 250 |     |     |     | 255 |     |     |
| --- | --- | --- | --- | --- | --- | --- | --- | --- | --- | --- | --- | --- | --- |
| His | Leu | Ala | Arg 260 | His | Leu | Gln | Glu | Asn 265 | Thr | Gln | Ser | His | Met 270 | Arg | Met |
| Leu | Ala | Gln 275 | Ala | Val | His | Ser | Leu 280 | Ser | Val | Ile | Pro | Asp 285 | Ser | Gly | Tyr |
| Ile | Ser 290 | Glu | Val | Arg | Asn | Phe 295 | Gln | Glu | Thr | Ile | His 300 | Gln | Leu | Glu | Gly |
| Arg 305 | Leu | Val | Arg | Gln | Asp 310 | His | Gln | Ile | Arg | Glu 315 | Leu | Thr | Ala | Lys | Met 320 |
| Glu | Thr | Gln | Ser | Met 325 | Tyr | Val | Ser | Glu | Leu 330 | Lys | Arg | Thr | Ile | Arg 335 | Thr |
| Leu | Glu | Asp | Lys 340 | Val | Ala | Glu | Ile | Glu 345 | Ala | Gln | Gln | Cys | Asn 350 | Gly | Ile |
| Tyr | Ile | Trp 355 | Lys | Ile | Gly | Asn | Phe 360 | Gly | Met | His | Leu | Lys 365 | Cys | Gln | Glu |
| Glu | Glu 370 | Lys | Pro | Val | Val | Ile 375 | His | Ser | Pro | Gly | Phe 380 | Tyr | Thr | Gly | Lys |
| Pro 385 | Gly | Tyr | Lys | Leu | Cys 390 | Met | Arg | Leu | His | Leu 395 | Gln | Leu | Pro | Thr | Ala 400 |
| Gln | Arg | Cys | Ala | Asn 405 | Tyr | Ile | Ser | Leu | Phe 410 | Val | His | Thr | Met | Gln 415 | Gly |
| Glu | Tyr | Asp | Ser 420 | His | Leu | Pro | Trp | Pro 425 | Phe | Gln | Gly | Thr | Ile 430 | Arg | Leu |
| Thr | Ile | Leu 435 | Asp | Gln | Ser | Glu | Ala 440 | Pro | Val | Arg | Gln | Asn 445 | His | Glu | Glu |
| Ile | Met 450 | Asp | Ala | Lys | Pro | Glu 455 | Leu | Leu | Ala | Phe | Gln 460 | Arg | Pro | Thr | Ile |
| Pro 465 | Arg | Asn | Pro | Lys | Gly 470 | Phe | Gly | Tyr | Val | Thr 475 | Phe | Met | His | Leu | Glu 480 |
| Ala | Leu | Arg | Gln | Arg 485 | Thr | Phe | Ile | Lys | Asp 490 | Asp | Thr | Leu | Leu | Val 495 | Arg |
| Cys | Glu | Val | Ser 500 | Thr | Arg | Phe | Asp | Met 505 | Gly | Ser | Leu | Arg | Arg 510 | Glu | Gly |
| Phe | Gln | Pro 515 | Arg | Ser | Thr | Asp | Ala 520 | Gly | Val |     |     |     |     |     |     |